(12) United States Patent
Jimenez et al.

(10) Patent No.: US 7,254,857 B2
(45) Date of Patent: Aug. 14, 2007

(54) POWER TOOTHBRUSH WITH UNIQUE HANDLE

(75) Inventors: Eduardo Jimenez, Manalapan, NJ (US); John Gatzemeyer, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 11/155,858

(22) Filed: Jun. 17, 2005

(65) Prior Publication Data

US 2005/0283929 A1 Dec. 29, 2005

Related U.S. Application Data

(63) Continuation of application No. PCT/US03/39540, filed on Dec. 12, 2003.

(60) Provisional application No. 60/434,106, filed on Dec. 17, 2002.

(51) Int. Cl.
*A61C 17/22* (2006.01)
*A46B 13/02* (2006.01)

(52) U.S. Cl. .......................... 15/22.1; 15/28
(58) Field of Classification Search .............. 15/22.1, 15/23, 28, 97.1; D4/138
See application file for complete search history.

(56) References Cited

U.S. PATENT DOCUMENTS

| D210,348 | S | * | 3/1968 | Levin ......................... D4/138 |
| 4,672,706 | A | * | 6/1987 | Hill ............................ 15/167.1 |
| 4,983,080 | A | | 1/1991 | Somers et al. |
| 5,301,381 | A | | 4/1994 | Klupt |
| 5,381,576 | A | | 1/1995 | Hwang |
| 5,625,916 | A | | 5/1997 | McDougall |
| 6,076,223 | A | | 6/2000 | Dair et al. |
| 6,202,242 | B1 | | 3/2001 | Salmon et al. |
| 6,367,112 | B1 | * | 4/2002 | Moskovich et al. ....... 15/167.1 |
| D459,087 | S | * | 6/2002 | Pfleger ....................... D4/104 |

* cited by examiner

*Primary Examiner*—Randall Chin
(74) *Attorney, Agent, or Firm*—Michael Wallace, Jr.

(57) ABSTRACT

A powered toothbrush is provided and includes a handle portion having a neck formed at one end and a head coupled to the neck. The handle portion is adapted to receive a pair of batteries therein. The head includes a base, and one or more carriers coupled to the base. At least one of the carriers is operatively connected to a drive for moving the one or more coupled carriers in respective directions. The one or more carriers have bristles, elastomeric cleaning members, or a combination thereof extending outwardly therefrom. The pair of batteries are positioned at a predetermined angle relative to a face of the carrier.

4 Claims, 8 Drawing Sheets

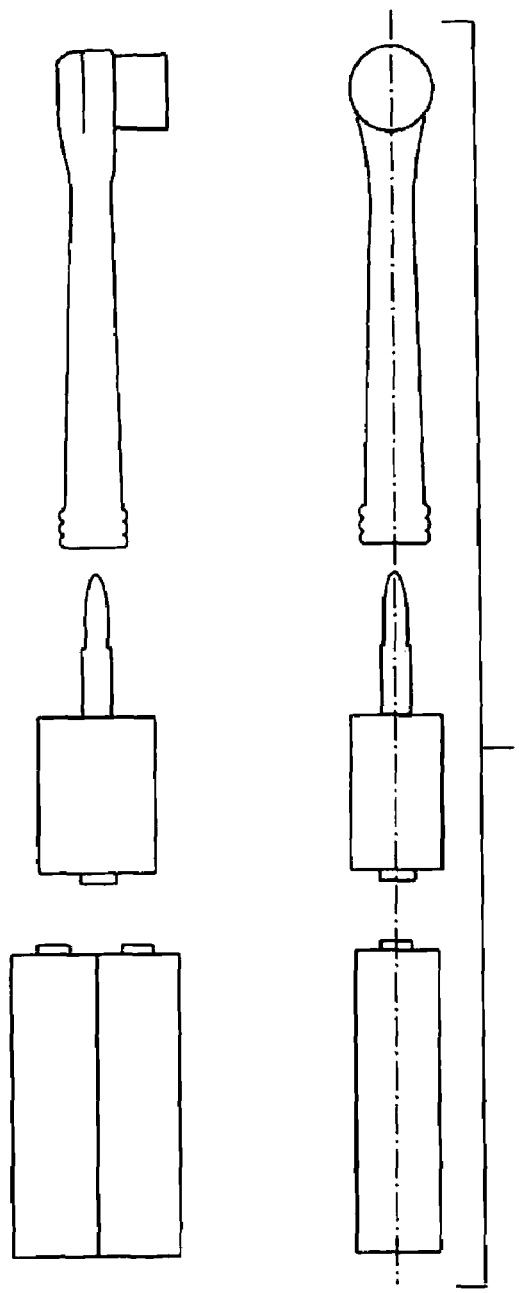
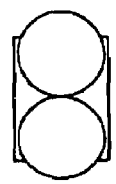
FIG. 2C
PRIOR ART
FIG. 2A
PRIOR ART
FIG. 2B
PRIOR ART

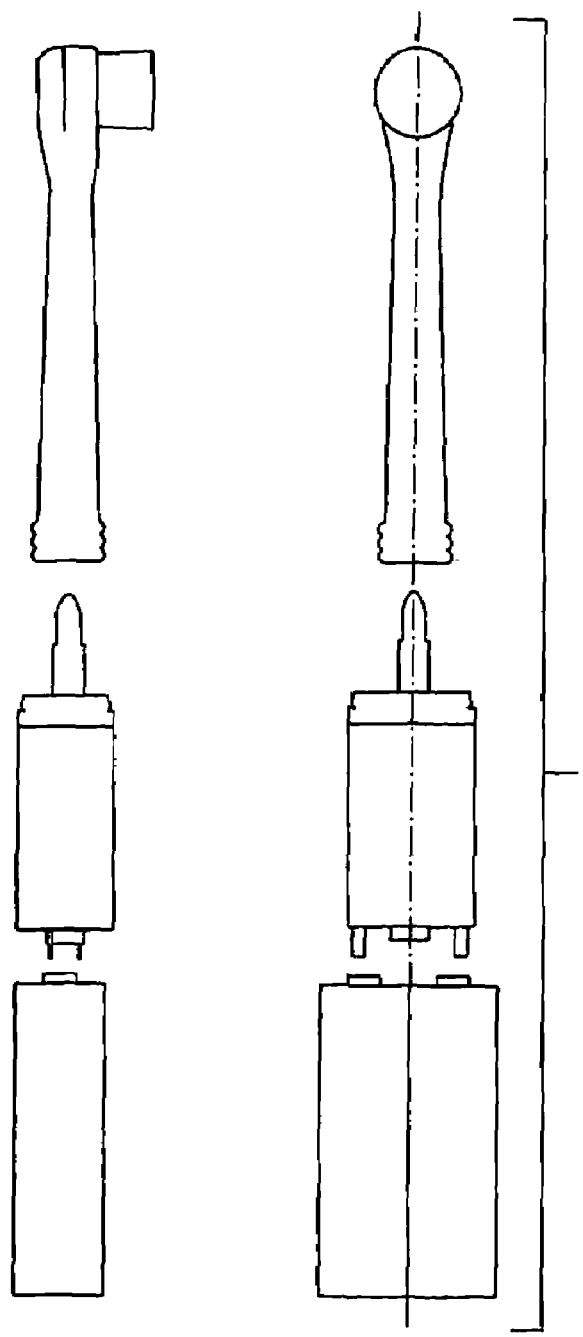
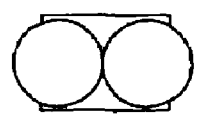
FIG. 3A
PRIOR ART
FIG. 3B
PRIOR ART
FIG. 3C
PRIOR ART

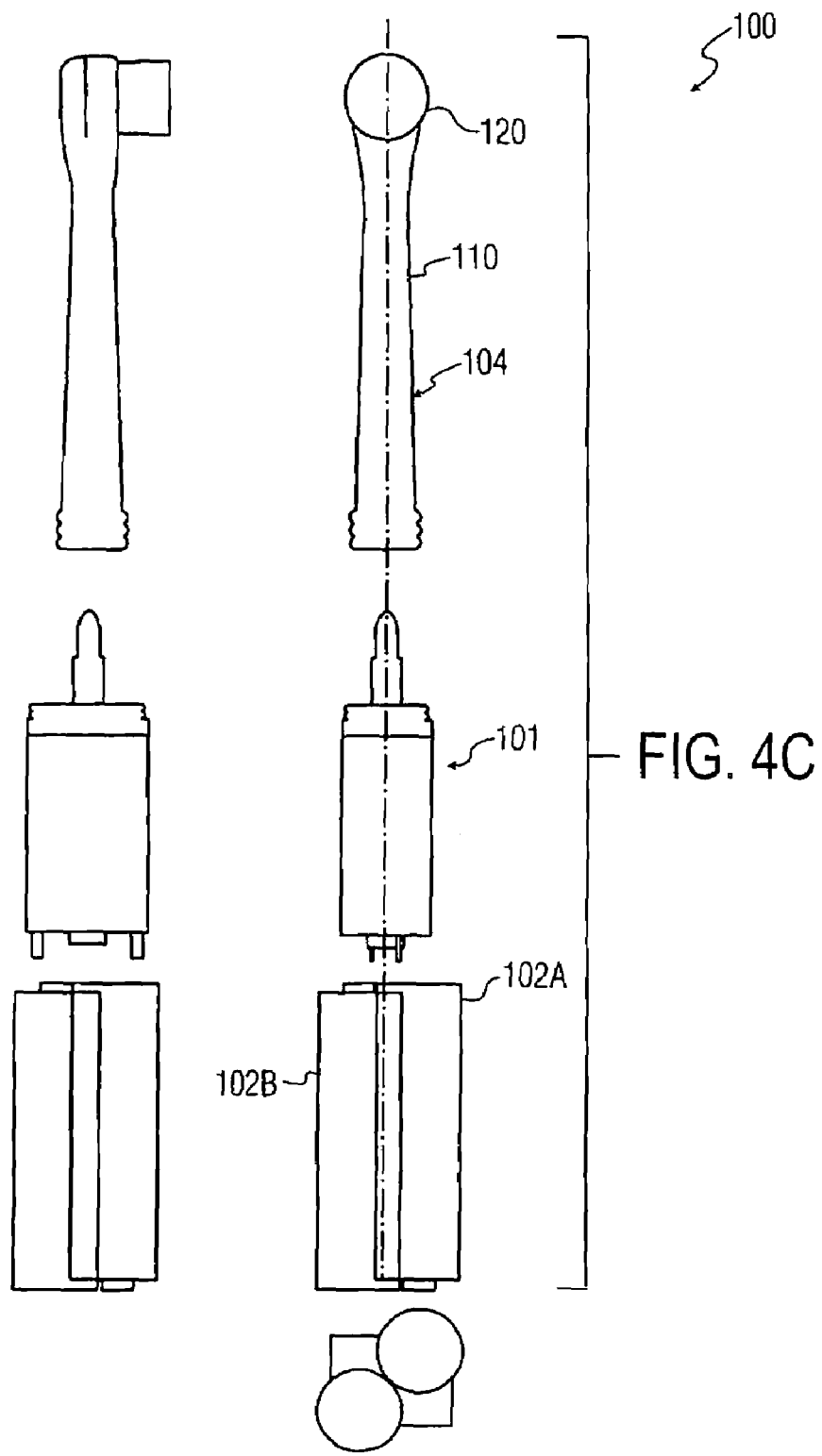

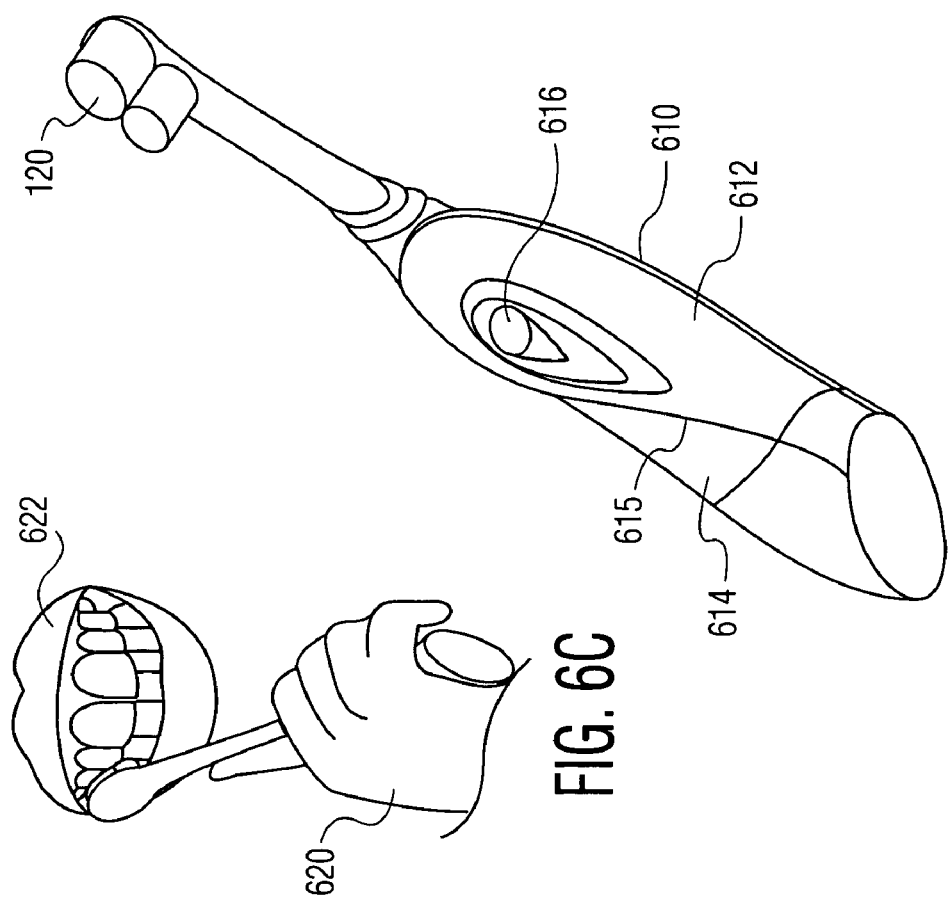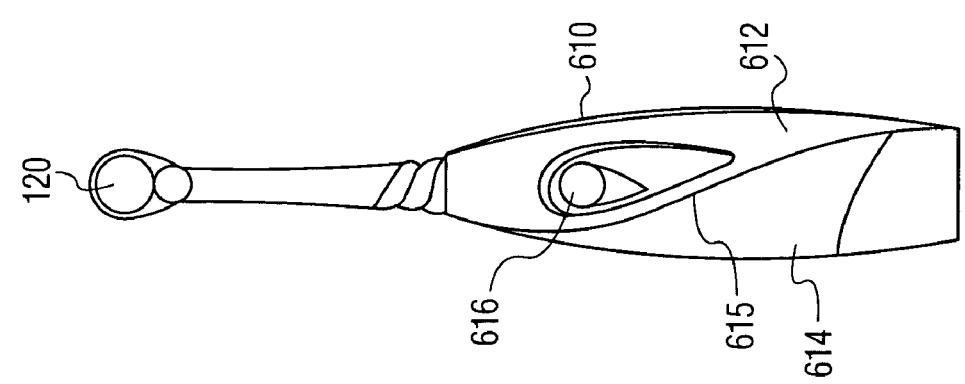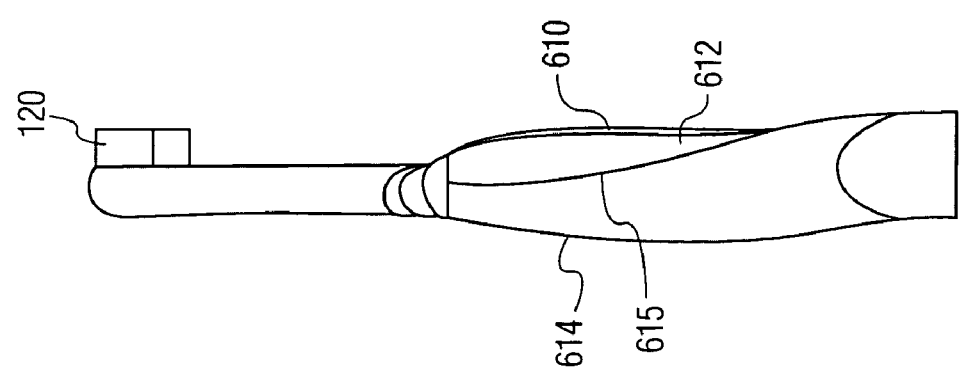

in a compact conical or cylindrical pattern on a generally circular, disk-shaped bristle carrier. The powered toothbrush heads are traditionally compact, generally oval in shape and heads are produced with a flat trimmed bristle pattern. Alternatively, other head shapes and bristle patterns are available.

POWER TOOTHBRUSH WITH UNIQUE HANDLE

CROSS-REFERENCE TO RELATED APPLICATIONS

This application is a continuation of co-pending PCT Application No. PCT/US2003/39540 (designating the U.S.), filed Dec. 12, 2003, which claims priority of U.S. Provisional Application Ser. No. 60/434,106, filed Dec. 17, 2002. The contents of the above-noted applications are each expressly incorporated herein by reference

BACKGROUND OF THE INVENTION

1. Field of the Invention

The present invention relates to powered toothbrushes, and more particularly, to a toothbrush having a unique handle and a unique relative positioning of conventional batteries to provide a more comfortable and easier to grip handle resulting in additional oral health benefits to the user.

2. Discussion of Related Art

Toothbrushes provide many oral hygiene benefits. For example, toothbrushes remove plaque and food debris to help avoid tooth decay and disease. They remove stained pellicle from the surface of each tooth to help whiten the teeth. Also, the bristles combined with the brushing motion massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, generally in combination with manual movement of toothbrush by the user, provide superior cleaning than manual toothbrushes. Typically, powered toothbrushes are powered by disposable or rechargeable batteries that power an electric motor that in turn drives toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaw, and each row of teeth consequently has a convex outer curve and a concave inner curve. Individual teeth often have extremely complex surfaces, with areas that may be flat, concave, or convex. The more precise conformation between the bristles and the tooth surface, the more effective toothbrush may be in cleaning, whitening and/or stimulating.

Known powered toothbrushes typically arrange the bristles in a compact conical or cylindrical pattern on a generally circular, disk-shaped bristle carrier. The powered toothbrush heads are traditionally compact, generally oval in shape and heads are produced with a flat trimmed bristle pattern. Alternatively, other head shapes and bristle patterns are available.

One example of a powered toothbrush is depicted in U.S. Pat. No. 5,625,916 to McDougall, which is hereby incorporated by reference in its entirety. Toothbrush shown in McDougall has a disc-shaped bristle carrier. The bristle carrier, and thus the bristles, are driven in a vibrating or oscillating manner. This type of toothbrush is described herein with reference to FIGS. 1A-1C. A toothbrush 5 includes a handle portion 10 at a proximal end of toothbrush 5 and a head 11 at a distal end of toothbrush 5. Handle portion 10 has compartments for containing a powered motor 14 and batteries 15 and 16. Head 11 includes a generally circular bristle holder (carrier) 13. A rotatable shaft 12 extends from the motor 14 to head 11. A shaft coupling 17 may be located along the shaft 12 and configured to provide for the shaft 12 to be separated at a point between the motor 14 and head 11. This permits the shaft to be removed from toothbrush 5, e.g., for cleaning, servicing, or replacement.

Head 11 includes a post 18 that provides a rotational pivot axis for the bristle holder 13 containing bristle tufts 19. The distal end of the shaft 12 has a journal or offset 20 that is radially displaced from the longitudinal axis of the shaft 12, which may be integrally formed therewith. The bristle holder 13 has a slot 22 that receives the offset 20. The offset 20 and slot 22 are configured so as to be oriented toward the intersection of the shaft 12 axis and the longitudinal axis of the post 18. When the motor 14 rotates the shaft 12, the motion of the offset 20 defines a circle about the shaft 12 axis and drivingly engages slot 22 such that the bristle holder 13 vibrates or oscillates about the post 18 axis through a rotational angle A. The rotational angle A is defined by the displacement of the offset 20 from the shaft 12 axis relative to the diameter of the bristle holder 13.

Although powered toothbrushes such as those described immediately above provide advantages over manual toothbrushes, they are subject to various limitations. Providing sufficient power for the toothbrush to operate requires substantial battery power, and consequently size. Typically, these batteries have been provided as a pair of batteries positioned one on top of the other in a coaxial relationship. While this configuration results in a thin handle portion, the handle portion may become unduly long, thus making it difficult for a user to handle the toothbrush.

One attempt to overcome the limitations associated with this battery configuration is to place the pair of batteries in the handle side by side, either along a plane positioned perpendicular to the face of the bristle carrier, or along a plane coplanar with the face of the bristle carrier. Such configurations are shown in FIGS. 2 and 3, respectively. Such configurations, however, limit the ability to shape the handle into a shape that is comfortable to the user and assists in allowing the user to properly grip the handle of the toothbrush. Therefore, a toothbrush including such a restricted battery positioning limits the overall effectiveness of the toothbrush.

Thus, there is a need in the art for a powered toothbrush with a more advantageous handle structure to improve the overall effectiveness of such a toothbrush. There is further a need for such improved toothbrushes to be comparable in manufacturing and purchasing costs as known powered toothbrushes.

SUMMARY OF THE INVENTION

A powered toothbrush is provided and includes a handle portion at a proximal end and either a fixed head or a linkage for receiving a removable head at a distal end thereof. A neck is further formed between the handle portion and the head.

The head may include only one, or two distinct movable parts that each and together provide oral health benefits, each being adapted to have a number of bristles or elastomeric cleaning members extending therefrom adapted to contact surfaces of one or more teeth and surrounding areas. The powered toothbrush is further formed with a drive mechanism that imparts movement to the first movable part to deliver a cleaning, polishing, whitening action that supplements the cleaning efficiency of a typical powered toothbrush. The first movable part may in turn impart movement to the second movable part.

Additionally, a pair of batteries are preferably positioned at approximately + or −45° relative to a plane positioned perpendicularly to the face of the bristle carrier. This offset positioning of the pair of batteries allows for a more user-friendly handle design, including twists of the handle and other easy to grip portions without substantially increasing the size or weight of the toothbrush.

Other features and advantages of the present invention will be apparent from the foregoing detailed description when read in conjunction with the accompanying drawings.

The invention accordingly comprises the several steps and the relation of one or more of such steps with respect to each of the others, and the apparatus embodying features of construction, combination(s) of elements and arrangement of parts that are adapted to effect such steps, all as exemplified in the following detailed disclosure, and the scope of the invention will be indicated in the claims.

BRIEF DESCRIPTION OF THE DRAWING FIGURES

For a more complete understanding of the invention, reference is made to the following description and accompanying drawings, in which:

FIGS. 2A and 2C are front and side exploded elevational views, respectively, and FIG. 2B is a bottom plan view of a conventional powered toothbrush depicting a pair of batteries positioned along a plane perpendicular to a face of a bristle carrier;

FIGS. 3A and 3C are front and side exploded elevational views, respectively, and FIG. 3B is a bottom plan view of a conventional powered toothbrush depicting a pair of batteries positioned along a plane coplanar with a face of a bristle carrier;

FIGS. 4A and 4C are front and side exploded elevational views, respectively, and FIG. 4B is a bottom plan view of a powered toothbrush having its batteries positioned at approximately 45° relative to a plane positioned perpendicularly to the face of the bristle carrier constructed in accordance with the invention;

FIGS. 5A and 5C are front and side exploded elevational views, respectively, and FIG. 5B is a bottom plan view of a powered toothbrush having its batteries positioned at approximately −45° relative to a plane positioned perpendicularly to the face of the bristle carrier constructed in accordance with the invention;

Figures 7A, 7B, 7C:
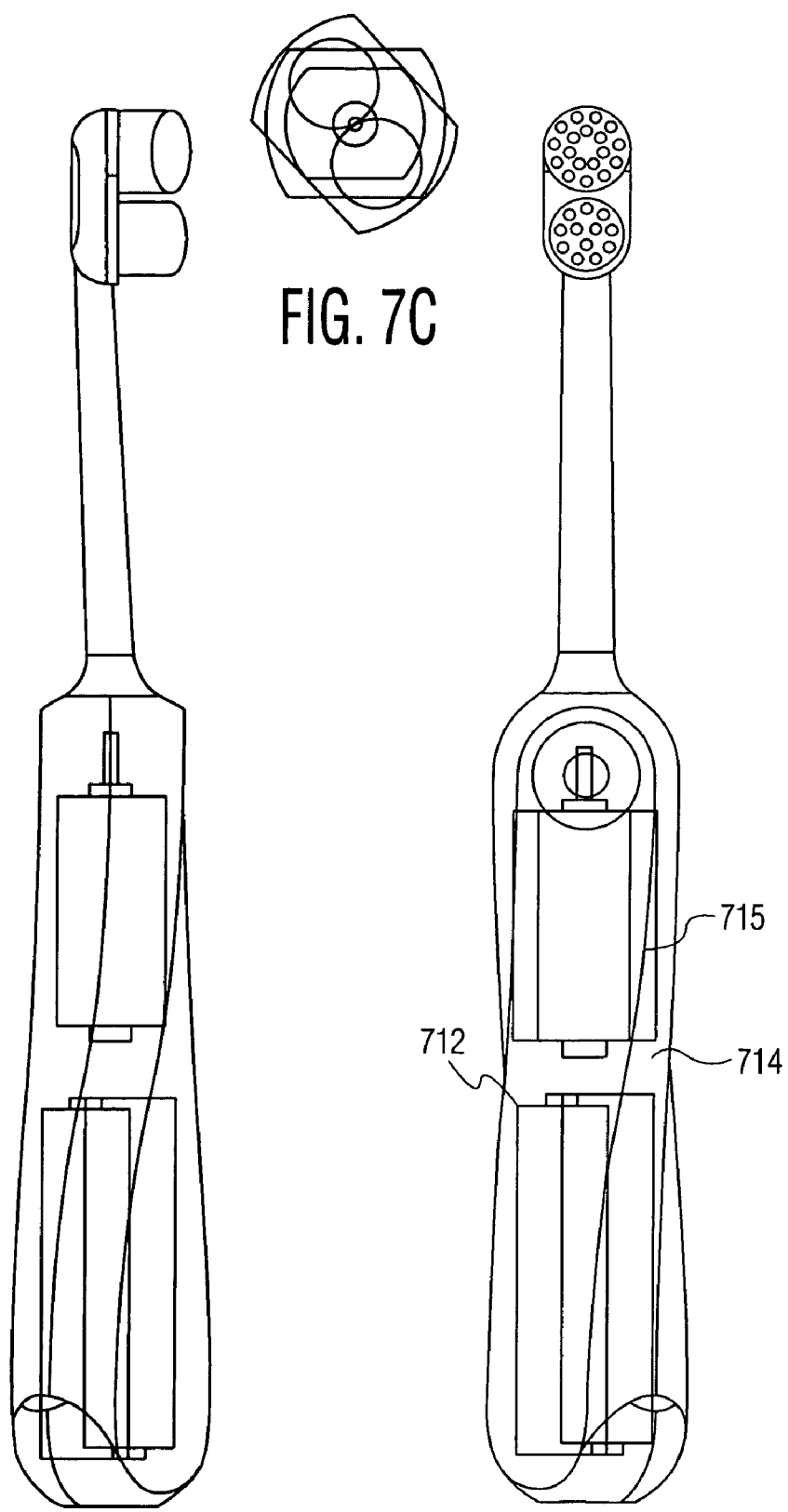

FIGS. 6A, 6B, 6C, and 6D are perspective views of a twisted form handle made possible by, and constructed in accordance with the invention; and FIGS. 7A and 7B are front and side elevational views, respectively, and FIG. 7C is a bottom view of a powered toothbrush constructed with a twisted form handle made possible by, and constructed in accordance with the invention.

DETAILED DESCRIPTION OF CERTAIN PREFERRED EMBODIMENTS OF THE PRESENT INVENTION

Referring first to FIGS. 4A-4C, an exemplary powered toothbrush according to a first embodiment of the invention is illustrated and generally indicated at 100. Toothbrush 100 includes a handle (not shown) at a proximal end thereof that defines an interior compartment (not illustrated) for housing various toothbrush components. The interior compartment of the handle typically houses, in addition to other components, a power source. This power source typically comprises two standard size batteries. Thus, the size and shape of the handle has traditionally been limited by the required power. The interior of the toothbrush constructed in accordance with the invention includes at least a motor and a pair of batteries 102A and 102B. Toothbrush 100 further comprises a brush section 104 that is defined by a neck 110 that terminates in a head 120 at a distal end of toothbrush 100.

Figure 1A:
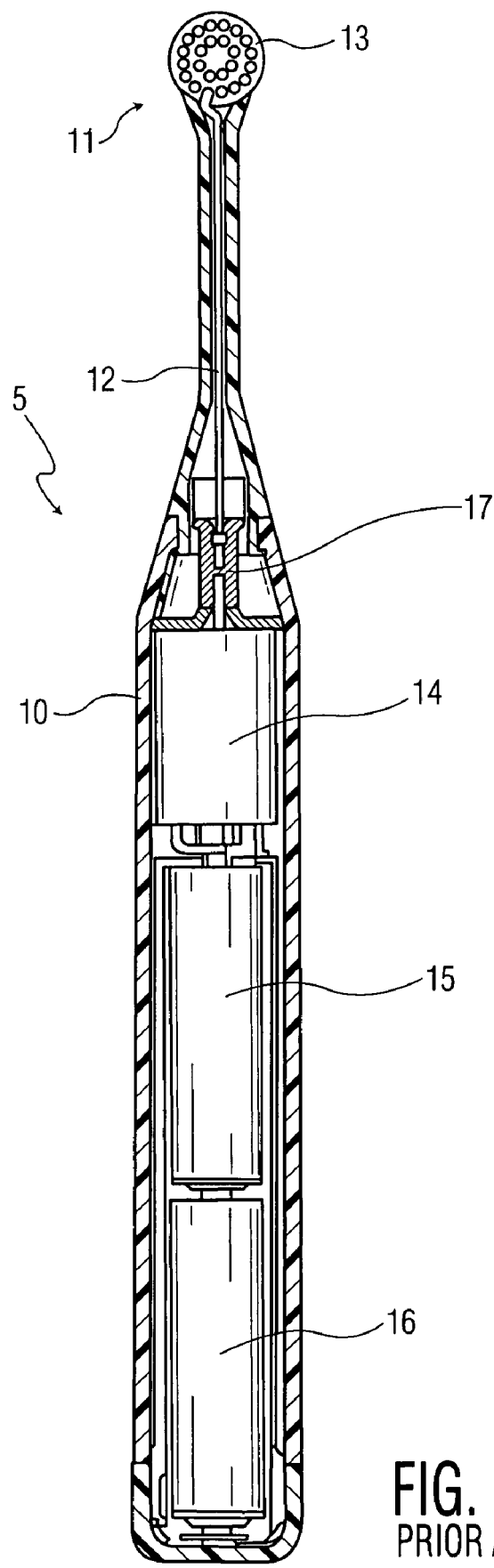
FIG. 1A is a front partial cross-sectional view of a conventional powered toothbrush including a head.
Figure 1B:
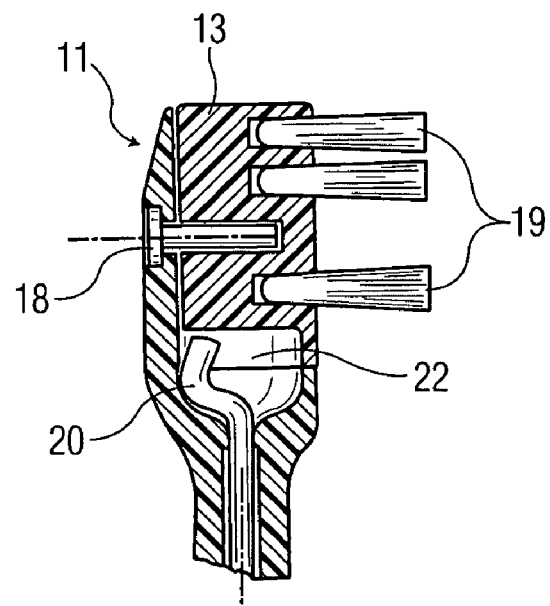
FIG. 1B is a partial side cross-sectional view of the toothbrush head of FIG. 1A.
Figure 1C:
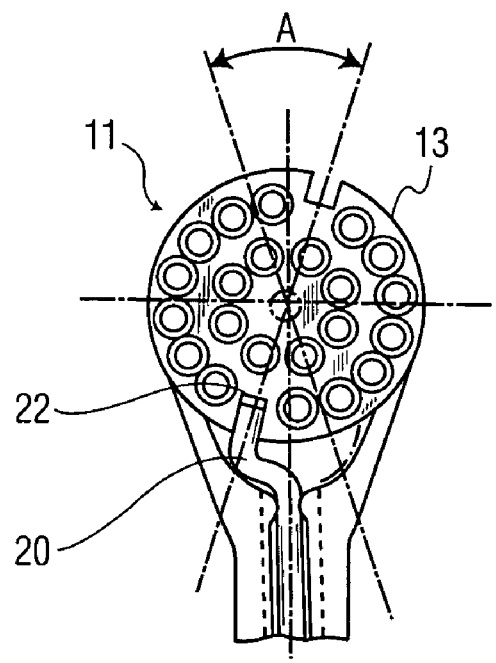
FIG. 1C is a partial front cross-sectional view of the toothbrush head of FIG. 1A.
Figures 5A, 5B:
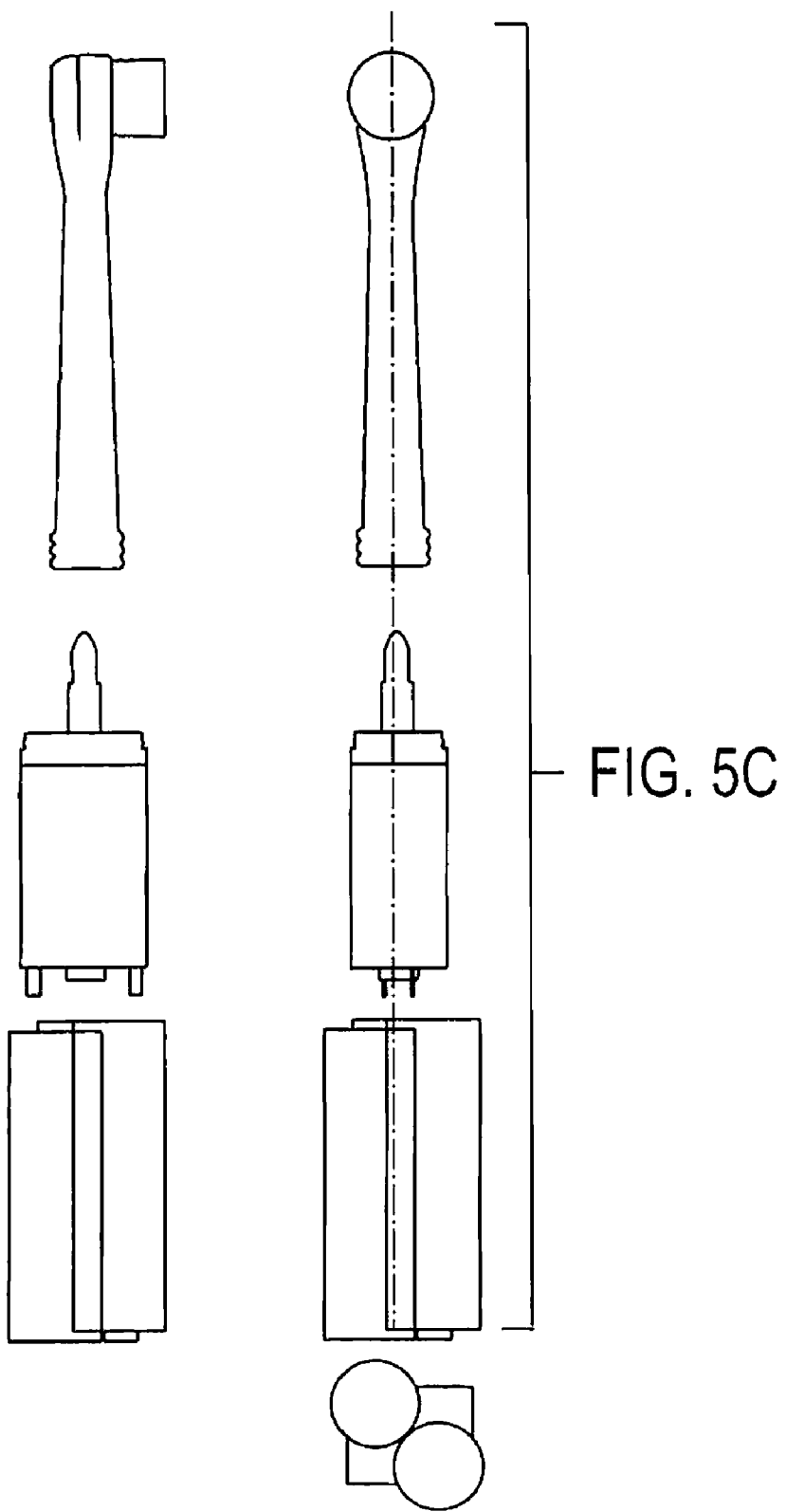

In accordance with the invention, the pair of batteries 102A and 102B is fit into a battery compartment housing (not shown) of the handle purposefully designed to receive the pair of batteries in a 45° offset configuration. As is shown in FIG. 4B, these batteries are provided at a 45° angle relative to a plane positioned perpendicular to the face of head 120. In such a configuration, as will be explained below, the battery positioning produces a natural shape to a handle that is advantageous for a user to hold. The batteries may similarly be provided at a −45° angle (FIG. 5B) relative to a plane positioned perpendicular to the face of head 120, thereby resulting in a natural shape of a different configuration from that of FIGS. 3A-3C. Furthermore, while approximately a + or −45° offset is shown, other offsets may be utilized that provide desirable configurations of the handle portion of the powered toothbrush.

Such a handle configuration is depicted in (FIGS. 6A-6D). In FIGS. 6A-6D, the battery configuration of FIGS. 4A-4C are utilized wherein the batteries are provided at a 45° angle relative to a plane positioned perpendicular to the face of the toothbrush head. Thus, as is shown in FIG. 6A, a protruding portion 612 of handle 610 follows the general shape of the batteries housed within handle portion 610. Recessed portion 614 is recessed relative to protruding portion 612, also based upon the positioning of the batteries inside the handle. A curved surface 615 separates the two, and preferably forms a guide point to be held by the hand of a user. A control button 616 is also provided (FIG. 6B). As is further shown (in FIG. 6C), when a hand 620 of a user holds handle 610, the positioning of portions 612 and 614, along with surface 615 allow for an easy to hold handle, an preferably position head 120 of the powered toothbrush to easily line up with the user's teeth 622 without requiring the twisting of the wrist or forearm of the user. Thus, a sure grip and increased comfort may be provided.

FIGS. 7A, 7B and 7C show an embodiment of the invention having a pair of batteries provided at a −45° angle relative to a plane positioned perpendicular to the face of the toothbrush head. As compared to FIGS. 6A-6D, this toothbrush configuration might be provided for a user preferring to hold his or her hand for brushing at a different angle.

Because of the positioning of batteries 102A and 102B, a protruding portion 712 allows for the user's hand to be positioned further away from the head of the toothbrush. Recessed portion 714 is defined by surface 715 and provides an appropriate position for the user to rest his or her hand.

It will further be appreciated that the illustrated shapes of handle 102 and neck 110 are merely exemplary in nature and handle 102 and/or neck 110 can be formed to have any number of shapes in accordance with the offset positioning of batteries 102A and 102B to therefore provide a toothbrush that is easily gripped and held and easily manipulated by the user. For example, handle 102 may also include slightly recessed finger sections formed on opposite sides of handle 102. One recessed finger section may be designed to receive the thumb of one hand and the other recessed finger section may be designed to receive one or more other fingers of the same hand to thereby further assist the user in proper placement of the toothbrush in the user's hand. One or more of recessed finger sections may include ribs or another type of roughened surface to assist the user in gripping the toothbrush at the recessed finger sections.

The toothbrush according to the various embodiments disclosed herein can be made from any number of materials that are suitable for use in oral care products, such as toothbrushes, etc. For example, many of the components that are included in toothbrush are formed of plastic materials. Accordingly, the handle and head of the powered toothbrush may be molded from polyolefins such as polypropylenes and polyethylenes, polyamids such as nylons, and polyesters such as polyethylene terephthalate. Other suitable materials include polymethylmethacrylate, styrene acroylonitrate and cellulose esters, for example cellulose propionate.

When the tooth care elements are in the form of tufts of bristles, the bristles of can be made from a flexible material suitable for dental hygiene. Generally, materials suitable for bristles are polyamides such as nylon or polyesters such as polybutylene terephthalate. When the tooth care elements are in the form of elastomeric members, they can be made from any number of suitable elastomeric materials, such as a block copolymer. Preferred block copolymers include styrenes (for example styrene ethylene butadiene styrene, or styrene butadiene styrene), polyolefins (for example polypropylene/ethylene propylene diamine modified systems (i.e. synthetic rubber)), polyamides (for example polyamide (2 or polyamide 6), polyesters (for example polyester ester or polyether ester), polyurethanes (for, example polyesterurethane, polyetherurethane or polyesteretherurethane).

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A powered toothbrush comprising:
   a handle portion being formed with a neck at a first end thereof and an interior compartment formed therein at a second end thereof for receiving no more than a single pair of batteries, the second end being disposed substantially opposite to the first end;
   a head coupled to the neck, the head further including:
   a base; and
   one or more carriers coupled to the base, at least one of the carriers being operatively connected to a drive member for moving the one or more coupled carriers in respective directions,
   wherein the interior compartment is arranged such that each battery of the single pair of batteries received in the interior compartment is generally aligned along a longitudinal axis with said neck and a face of said carrier, said pair of batteries being generally positioned along said longitudinal axis at a predetermined angle from said face of said carrier; wherein said angle is approximately 45°.

2. The powered toothbrush of claim 1, wherein said handle is formed with a contoured surface following a general shape as designated by the position of the batteries.

3. The powered toothbrush of claim 2, wherein said contoured surface includes a longitudinal twist along the handle portion extending from said neck to said interior compartment.

4. The powered toothbrush of claim 1, wherein said handle is formed with a contoured surface following a general shape as designated by the position of the batteries received in the interior compartment, said contoured surface including a longitudinal twist along the handle portion extending from the neck to said interior compartment.

* * * * *